US00PP25503P2

(12) United States Plant Patent
Kinney

(10) Patent No.: US PP25,503 P2
(45) Date of Patent: May 5, 2015

(54) ***TSUGA* PLANT NAMED 'MONKINN'**

(50) Latin Name: *Tsuga canadensis*
Varietal Denomination: MonKinn

(71) Applicant: Ron Damien Kinney, Dayton, OR (US)

(72) Inventor: Ron Damien Kinney, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 116 days.

(21) Appl. No.: 13/986,829

(22) Filed: Jun. 10, 2013

(51) Int. Cl.
*A01H 7/00* (2006.01)

(52) U.S. Cl.
USPC ..... Plt./213

(58) Field of Classification Search
CPC ..... A01H 7/00; A01H 5/00; A01H 5/04
USPC ..... Plt./213
See application file for complete search history.

*Primary Examiner* — June Hwu
(74) *Attorney, Agent, or Firm* — C. A. Whealy

(57) ABSTRACT

A new and distinct cultivar of *Tsuga* plant named 'MonKinn', characterized by its compact, upright to arching and mounding plant habit; vigorous and moderately fast-growing growth habit; freely branching habit, dense and bushy plant form; bright yellow green-colored developing leaves; and tolerance to full sunlight conditions.

1 Drawing Sheet

Botanical designation: *Tsuga canadensis.*
Cultivar denomination: 'MONKINN'.

BACKGROUND OF THE INVENTION

The present Invention relates to a new and distinct cultivar of *Tsuga* plant, botanically known as *Tsuga canadensis*, and hereinafter referred to by the name 'MonKinn'.

The new *Tsuga* plant is a naturally-occurring whole plant mutation of an unnamed selection of *Tsuga canadensis*, not patented. The new *Tsuga* plant was discovered and selected by the Inventor as a single plant in July, 2000 from within a population of plants of the unnamed selection in a controlled outdoor nursery environment in Dayton, Oreg.

Asexual reproduction of the new *Tsuga* plant by cuttings in a controlled environment in Dayton, Oreg. since December 2007 has shown that the unique features of this new *Tsuga* plant are stable and reproduced true to type in successive generations.

SUMMARY OF THE INVENTION

Plants of the new *Tsuga* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'MonKinn'. These characteristics in combination distinguish 'MonKinn' as a new and distinct *Tsuga* plant:

1. Compact, upright to arching and mounding plant habit.
2. Vigorous and moderately fast-growing growth habit.
3. Freely branching habit, dense and bushy plant form.
4. Bright yellow green-colored developing leaves.
5. Tolerant to full sunlight conditions.

Plants of the new *Tsuga* are most similar to plants of the unnamed parent selection. In side-by-side comparison, plants of the new *Tsuga* differ primarily from plants of the unnamed parent selection in the following characteristics:

1. Plants of the new *Tsuga* are much more compact than plants of the unnamed parent selection.
2. Plants of the new *Tsuga* are arching and mounding whereas plants of the unnamed parent selection are pyramidal in form.
3. Plants of the new *Tsuga* and the unnamed parent selection differ in leaf color as plants of the unnamed parent selection have dark green-colored leaves.

Plants of the new Cedar can also be compared to plants of *Tsuga canadensis* 'Jeddeloh', not patented. Plants of the new *Tsuga* differ from plants of 'Jeddeloh' in the following characteristics:

1. Plants of the new *Tsuga* are arching and mounding whereas plants of 'Jeddeloh' are low spreading and pendulous.
2. Plants of the new *Tsuga* and 'Jeddeloh' differ in leaf color as leaves of plants of 'Jeddeloh are medium green in color.

BRIEF DESCRIPTION OF THE PHOTOGRAPHS

The accompanying colored photographs illustrate the overall appearance of the new *Tsuga* plant showing the colors as true as it is reasonably possible to obtain in colored reproductions of this type. Colors in the photographs may differ slightly from the color values cited in the detailed botanical description which accurately describe the colors of the new *Tsuga* plant.

The photograph at the bottom of the sheet is a side perspective view of a typical plant of 'MonKinn' grown in a container.

The photograph at the top of the sheet is a close-up view of a typical plant of 'MonKinn'.

DETAILED BOTANICAL DESCRIPTION

Plants used for the aforementioned photographs and following observations and measurements were grown in twogallon containers in Dayton, Oreg. during the winter in an outdoor nursery and under cultural practices typical of commercial *Tsuga* plant production. During the production of the plants, day temperatures ranged from 4° C. to 32° C. and night temperatures ranged from −2° C. to 15° C. Plants were 33 months old when the photographs and description were taken. In the following description, color references are made to The Royal Horticultural Society Colour Chart, 2007 Edition, except where general terms of ordinary dictionary significance are used.

Botanical classification: *Tsuga canadensis* 'MonKinn'.

Parentage: Naturally-occurring whole plant mutation of an unnamed selection of *Tsuga canadensis*, not patented.

Propagation:

*Type*.—By cuttings.

*Time to initiate roots, winter*.—About two to three months at soil temperatures ranging from 16° C. to 24° C.

*Time to produce a rooted young plant, summer*.—About three months at soil temperatures ranging from 16° C. to 24° C.

*Root description*.—Medium in thickness, fibrous; white in color.

*Rooting habit*.—Moderately freely branching; medium density.

Plant description:

*Plant and growth habit*.—Compact, upright to arching and mounding evergreen shrub, nearly rounded plant habit; vigorous and moderately fast-growing growth habit.

*Branching habit*.—Freely branching with about ten lateral branches developing per plant; dense and bushy plant form; plants maintain their lower branches and foliage at the soil level.

*Plant height*.—About 35 cm.

*Plant diameter*.—About 46 cm.

*Lateral branch description*.—Length: About 32 cm. Diameter: About 6 mm. Internode length: About 1.8 cm to 2.5 cm. Texture, young branches: Pubescent. Texture, mature branches: Woody, slightly rough. Strength: Strong. Aspect: About 45 to 55° from vertical. Color, young branches: Close to 145A to 145B. Color, mature branches: Close to 199A.

*Leaf description*.—Arrangement: Alternate and opposite; simple. Length: About 1.4 cm. Width: About 2 mm. Shape: Acicular, flattened. Apex: Acute. Base: Attenuate. Margin, developing leaves: Entire. Margin, fully expanded leaves: Mostly entire and finely denticulate. Texture, upper and lower surface: Smooth, glabrous. Venation pattern: Single midvein. Color: Developing leaves, upper surface: Close to 150C to 150D. Developing leaves, lower surface: Close to 151A. Fully expanded leaves, upper surface: Close to 146B; venation, close to 146A; leaves tolerant to full sunlight conditions. Fully expanded leaves, lower surface: Close to 146D; narrow longitudinal stripes, close to 148D; venation, close to 148B. Petioles: Length: Less than 1 mm. Diameter: Less than 1 mm. Texture, upper and lower surfaces: Smooth, glabrous. Color, upper and lower surfaces: Close to 145D. Cone description: Cone development has not been observed on plants of the new *Tsuga*.

Disease & pest resistance: Plants of the new *Tsuga* have not been noted to be resistant to pathogens or pests common to *Tsuga* plants.

Weather tolerance: Plants of the new *Tsuga* plant have been observed to be tolerant to drought, rain, wind and full sunlight. Plants of the new *Tsuga* are hardy to USDA Hardiness Zones 4.

It is claimed:

1. A new and distinct *Tsuga* plant named 'MonKinn' as illustrated and described.

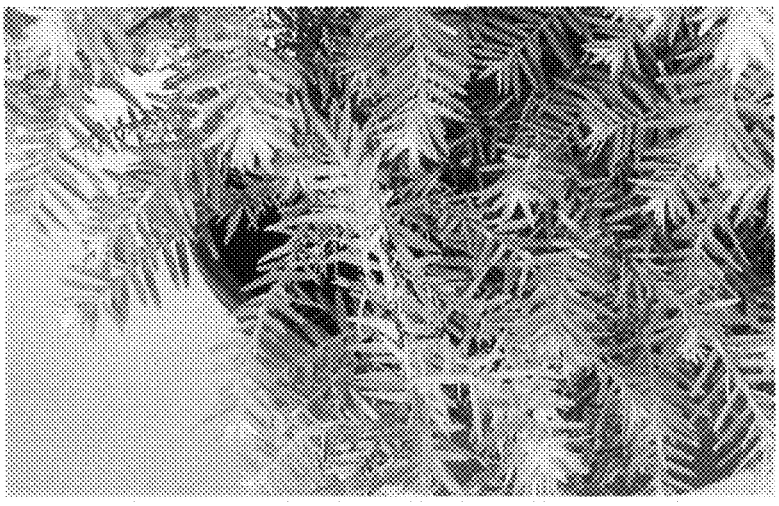
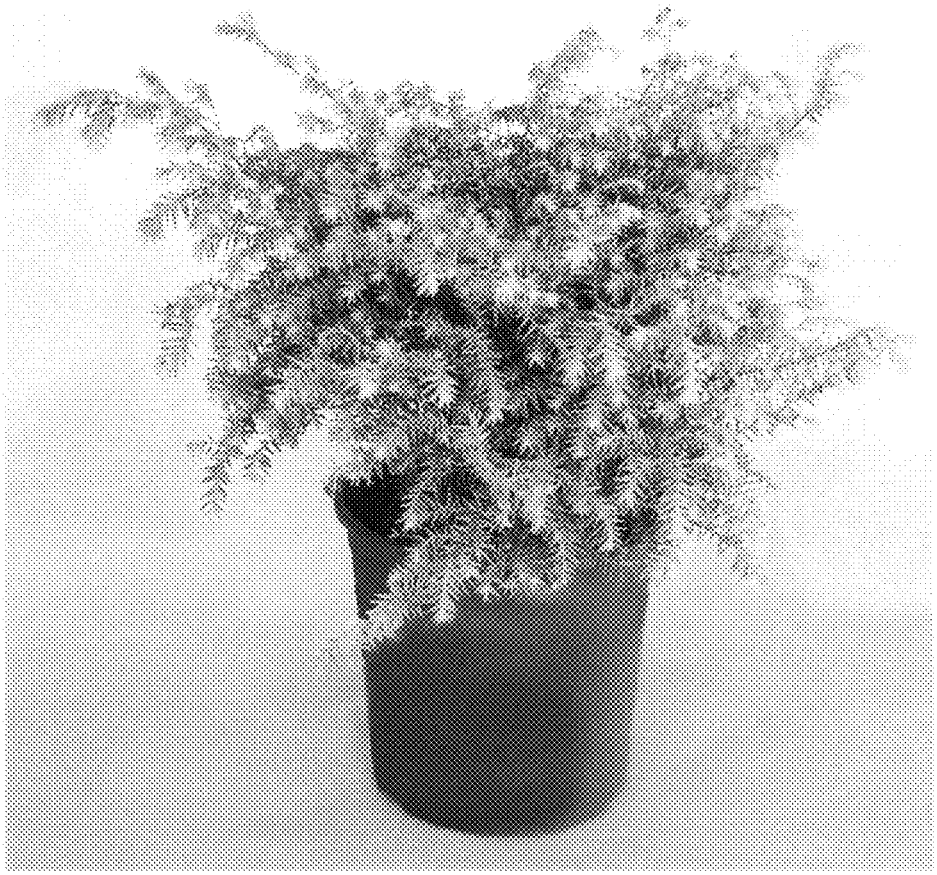

* * * * *